(12) United States Patent
Shiono et al.

(10) Patent No.: US 7,862,981 B2
(45) Date of Patent: *Jan. 4, 2011

(54) COMPOUND, POSITIVE RESIST COMPOSITION AND METHOD OF FORMING RESIST PATTERN

(75) Inventors: Daiju Shiono, Kawasaki (JP); Taku Hirayama, Kawasaki (JP); Hideo Hada, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 338 days.

This patent is subject to a terminal disclaimer.

(21) Appl. No.: 11/917,458

(22) PCT Filed: Jun. 7, 2006

(86) PCT No.: PCT/JP2006/311443

§ 371 (c)(1), (2), (4) Date: Dec. 13, 2007

(87) PCT Pub. No.: WO2006/134814

PCT Pub. Date: Dec. 21, 2006

(65) Prior Publication Data

US 2010/0009284 A1 Jan. 14, 2010

(30) Foreign Application Priority Data

Jun. 17, 2005 (JP) ............................. 2005-177504

(51) Int. Cl.
G03C 1/00 (2006.01)
C07C 39/12 (2006.01)

(52) U.S. Cl. .................................. 430/270.1; 568/720

(58) Field of Classification Search .............. 430/270.1; 568/720

See application file for complete search history.

(56) References Cited

U.S. PATENT DOCUMENTS

| 5,658,706 | A | 8/1997 | Niki et al. |
| 5,693,452 | A | 12/1997 | Aoai et al. |
| 5,707,776 | A | 1/1998 | Kawabe et al. |
| 5,824,451 | A | 10/1998 | Aoai et al. |
| 5,837,420 | A | 11/1998 | Aoai et al. |
| 5,844,057 | A | 12/1998 | Watanabe et al. |
| 5,994,025 | A | 11/1999 | Iwasa et al. |
| 6,037,098 | A | 3/2000 | Aoai et al. |
| 6,106,993 | A | 8/2000 | Watanabe et al. |
| 6,197,473 | B1 | 3/2001 | Kihara et al. |
| 6,638,683 | B1 | 10/2003 | Tan et al. |
| 7,220,808 | B2 | 5/2007 | Yamagishi et al. |
| 7,504,196 | B2 | 3/2009 | Shiono et al. |
| 2002/0025495 | A1 | 2/2002 | Ogata et al. |
| 2002/0058205 | A1 | 5/2002 | Nakashima et al. |
| 2003/0232277 | A1 | 12/2003 | Sasaki et al. |
| 2004/0005512 | A1 | 1/2004 | Mizutani et al. |
| 2004/0234885 | A1 | 11/2004 | Watanabe et al. |
| 2005/0271971 | A1 | 12/2005 | Ueda et al. |
| 2007/0259273 | A1 | 11/2007 | Shiono et al. |
| 2007/0281243 | A1 | 12/2007 | Hirayama |
| 2008/0020288 | A1 | 1/2008 | Hirayama et al. |
| 2008/0145784 | A1 | 6/2008 | Shiono et al. |
| 2009/0162781 | A1 | 6/2009 | Shiono et al. |

FOREIGN PATENT DOCUMENTS

| JP | H05-061197 | 3/1993 |
| JP | H05-249681 | 9/1993 |
| JP | H06-059444 | 3/1994 |
| JP | H06-167811 | 6/1994 |
| JP | H06-266109 A | 9/1994 |
| JP | 08-193054 | 7/1996 |
| JP | H08-220740 | 8/1996 |
| JP | 08-262712 | 10/1996 |
| JP | H08-337616 | 12/1996 |
| JP | H09-005999 | 1/1997 |
| JP | H09-160246 | 6/1997 |
| JP | H09-211866 | 8/1997 |
| JP | H10-123703 A | 5/1998 |

(Continued)

OTHER PUBLICATIONS

International Search Report in connection with corresponding PCT application No. PCT/JP2006/311443, dated Jun. 7, 2006.

(Continued)

*Primary Examiner*—Cynthia H Kelly
*Assistant Examiner*—Connie P Johnson
(74) *Attorney, Agent, or Firm*—Knobbe, Martens, Olson & Bear, LLP

(57) ABSTRACT

A compound including a polyhydric phenol compound represented by general formula (I) shown below (wherein $R^{11}$ to $R^{17}$ each independently represents an alkyl group of 1 to 10 carbon atoms or aromatic hydrocarbon group which may contain a hetero atom in the structure thereof, and X represents an aliphatic cyclic group) and having a molecular weight of 300 to 2,500, in which some or all of the hydrogen atoms of the phenolic hydroxyl groups are substituted with acid dissociable, dissolution inhibiting groups; a positive resist composition containing the compound; and a method of forming a resist pattern using the positive resist composition.

(I)

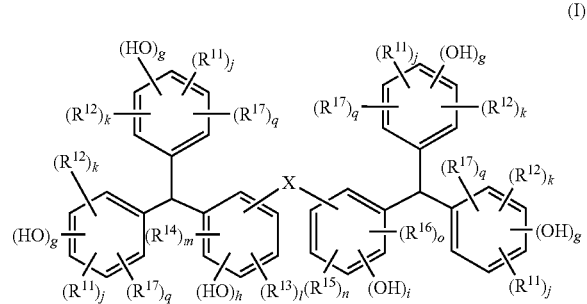

8 Claims, No Drawings

FOREIGN PATENT DOCUMENTS

| | | |
|---|---|---|
| JP | A 10-274845 | 10/1998 |
| JP | A-11-153863 | 6/1999 |
| JP | H11-167199 | 6/1999 |
| JP | H11-199533 | 7/1999 |
| JP | 2000-086584 | 3/2000 |
| JP | 2000-305270 | 11/2000 |
| JP | 2000-330282 | 11/2000 |
| JP | 2001-312055 | 11/2001 |
| JP | 2002-099088 | 4/2002 |
| JP | 2002-099089 | 4/2002 |
| JP | 2002-221787 | 8/2002 |
| JP | A-2002-328473 | 11/2002 |
| JP | A-2003-084437 | 3/2003 |
| JP | 2003-183227 | 7/2003 |
| JP | 2003-260881 | 9/2003 |
| JP | 2004-062049 | 2/2004 |
| JP | 2004-125835 | 4/2004 |
| JP | 2004-151605 | 5/2004 |
| JP | A-2004-191913 | 7/2004 |
| JP | 2004-302440 | 10/2004 |
| JP | 2004-359590 | 12/2004 |
| JP | 2002-055452 | 2/2005 |
| JP | 2005-089387 | 4/2005 |
| JP | 2005-091909 | 4/2005 |
| JP | 2005-309421 | 11/2005 |
| KR | 0231242 | 5/1997 |
| KR | 2001-0088341 | 9/2001 |
| KR | 10-0406242 | 11/2003 |
| TW | 200302397 A | 8/2003 |
| TW | 200617602 | 6/2006 |
| WO | WO 2006/046383 | 5/2006 |

OTHER PUBLICATIONS

European Search Report issued on counterpart European Patent Application No. EP 05788289.6, dated Jul. 26, 2010.

Hirayama, T., et al. "Depth Profile and Line-Edge Roughness of Low-Molecular-Weight Amorphous Electron Beam Resists", The Japan Journal of Applied Physics, vol. 44, No. 7B, 2005, pp. 5484-5488 (published on Jul. 26, 2005).

Hirayama et al. "Development of Electron Beam Resists Based on Amorphous Polyphenols with Low Molecular Weight and Narrow Dispersion," Proceedings of SPIE, vol. 5753, pp. 738-745.

Hirayama et al., Journal of Photopolymer Science and Technology, vol. 17, No. 3, 435-440, (2004).

Yamaguchi et al., Linewidth fluctuations caused by polymer aggregates in resist films, Journal of Photopolymer Science and Technology, vol. 10, No. 4, pp. 635-640, (1997).

Hirayama et al, "Development of Amorphous PolyPhenol Resists with Low Molecular Weight and Narrow Dispersion for EB Lithography", IEEE Xplore, Oct. 22, 2004, pp. 10-11.

COMPOUND, POSITIVE RESIST COMPOSITION AND METHOD OF FORMING RESIST PATTERN

RELATED APPLICATIONS

This application is the U.S. National Phase filing under 35 U.S.C. §371 of PCT/JP2006/311443, filed June 7, 2006, which designated the United States and was published in a language other than English, which claims priority under 35 U.S.C. §119(a)-(d) to Japanese Patent Application No. 2005-177504 filed June 17, 2005. The content of these applications is incorporated herein by reference in their entireties.

TECHNICAL FIELD

The present invention relates to a compound preferably used for a positive resist composition, a positive resist composition and a method of forming a resist pattern.

BACKGROUND ART

In recent years, in the production of semiconductor elements and liquid crystal display elements, advances in lithography techniques have lead to rapid progress in the field of miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now also starting to be introduced in mass production. Further, research is also being conducted into lithography techniques that use $F_2$ excimer lasers, electron beam, extreme ultraviolet radiation (EUV), X ray and the like as the light source (radiation source).

One example of a known resist that is capable of producing patterns of minute dimensions is a chemically amplified resist, which includes a base resin capable of forming a film and an acid generator that generates acid upon exposure. These chemically amplified resists include negative resists in which the alkali solubility of the exposed portions decreases, and positive resists in which the alkali solubility of the exposed portions increases.

Conventionally, polyhydroxystyrene (PHS) or derivative resins thereof in which the hydroxyl groups have been protected with acid-dissociable, dissolution-inhibiting groups (PHS-based resins), and copolymers derived from (meth) acrylate ester or derivative resins thereof in which the carboxyl groups have been protected with acid dissociable, dissolution inhibiting groups, have been used as the base resin component of chemically amplified resists.

However, when a pattern is formed using this type of pattern-forming material, a problem arises in that roughness may develop on the upper surface and side wall surfaces of the pattern. For example, the roughness on the side wall surfaces of the resist pattern called line edge roughness (LER) causes distortion around the periphery of the holes of a hole pattern and fluctuation of line width of a line and space pattern. As a result, adverse effects may be caused in the production of fine semiconductor devices.

This problem of surface roughness becomes more serious as the pattern size becomes smaller. Therefore, for example, in lithography using electron beam or EUV, very fine patterns of a few 10 nm is a goal, which means that an extremely low pattern roughness beyond the present pattern roughness is desired.

However, a polymer typically used as the base component has a molecular size (mean square radius of a molecule) as large as about a few nanometers. In the developing process of pattern formation, the resist generally exhibits a dissolution behavior corresponding to one molecule of the base component. For this reason, as long as such a polymer is used as the base component, it is extremely difficult to further reduce the roughness.

For solving the above-mentioned problems, resists using a low molecular weight material as the base component have been proposed as a material for achieving extremely low roughness. For example, in Patent Documents 1 and 2, there has been proposed a low molecular weight material having alkali soluble groups such as hydroxyl groups in which some or all of the alkali soluble groups are protected with acid dissociable, dissolution inhibiting groups. Such a low molecular weight material has a small molecular size as it has a low molecular weight, and hence, it is expected to be capable of reducing the roughness.

[Patent Document 1] Japanese Unexamined Patent Application, First Publication No. 2002-099088

[Patent Document 2] Japanese Unexamined Patent Application, First Publication No. 2002-099089

DISCLOSURE OF INVENTION

Problems to be Solved by the Invention

However, it was difficult to form a resist pattern with reduced roughness from such a material, for example, a fine pattern of no more than 90 nm, which can be put to practical use. For example, there were problems in that the pattern itself cannot be formed (pattern-forming ability is low), or even when a pattern could be formed, the roughness could not be sufficiently lowered, and the shape of the pattern cannot be maintained (pattern maintenance ability is low).

The present invention takes the above circumstances into consideration, with objects of providing a positive resist composition capable of forming a resist pattern with reduced roughness, a method of forming a resist pattern, and a compound which can be preferably used for the positive resist composition.

Means to Solve the Problems

As a result of extensive and intensive studies, the present inventors found that the above-mentioned problems can be solved by a compound including a polyhydric phenol compound having a specific structure and a specific molecular weight, in which the phenolic hydroxyl groups are protected with acid dissociable, dissolution inhibiting groups. The present invention has been completed based on this finding.

Specifically, a first aspect of the present invention is a compound including a polyhydric phenol compound represented by general formula (I) shown below and having a molecular weight of 300 to 2,500, in which some or all of the hydrogen atoms of the phenolic hydroxyl groups are substituted with acid dissociable, dissolution inhibiting groups:

[Chemical Formula I]

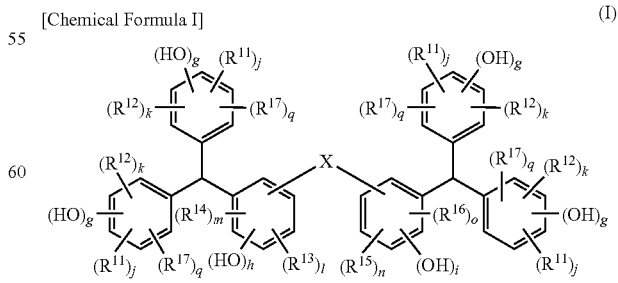

(I)

wherein $R^{11}$ to $R^{17}$ each independently represents an alkyl group of 1 to 10 carbon atoms or aromatic hydrocarbon group which may contain a hetero atom in the structure thereof; g and j each independently represents an integer of 1 or more, and k and q each independently represents 0 or an integer of 1 or more, with the proviso that g+j+k+q is 5 or less; h represents an integer of 1 or more, and l and m each independently represents 0 or an integer of 1 or more, with the proviso that h+l+m is 4 or less; i represents an integer of 1 or more, and n and o each independently represents 0 or an integer of 1 or more, with the proviso that i+n+o is 4 or less; and X represents an aliphatic cyclic group.

Further, a second aspect of the present invention is a positive resist composition including a base component (A) which exhibits increased alkali solubility under action of acid and an acid generator component (B) which generates acid upon exposure, the base component (A) including a compound (A1) including a polyhydric phenol compound represented by general formula (I) shown below and having a molecular weight of 300 to 2,500, in which some or all of the hydrogen atoms of the phenolic hydroxyl groups are substituted with acid dissociable, dissolution inhibiting groups:

EFFECT OF THE INVENTION

According to the present invention, there are provided a positive resist composition capable of forming a resist pattern with reduced roughness, a method of forming such a resist pattern, and a compound preferably used for the positive resist composition.

BEST MODE FOR CARRYING OUT THE INVENTION

<<Compound>>

The compound according to the first aspect of the present invention (hereafter, frequently referred to as "compound (A1)") includes a polyhydric phenol compound represented by general formula (I) shown above and having a molecular weight of 300 to 2,500, in which some or all of the hydrogen atoms of the phenolic hydroxyl groups are substituted with acid dissociable, dissolution inhibiting groups.

When the compound (A1) constitutes a positive resist composition with the acid generator component (B), the acid

[Chemical Formula 2]

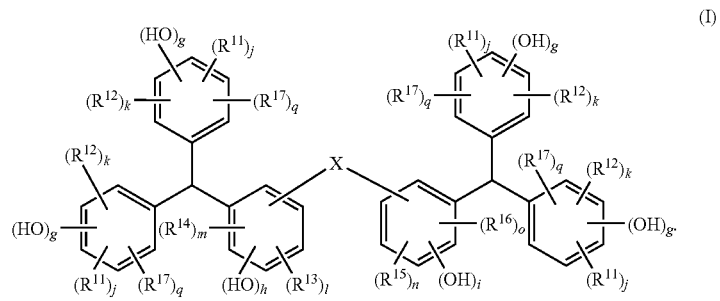

(I)

wherein $R^{11}$ to $R^{17}$ each independently represents an alkyl group of 1 to 10 carbon atoms or aromatic hydrocarbon group which may contain a hetero atom in the structure thereof; g and j each independently represents an integer of 1 or more, and k and q each independently represents 0 or an integer of 1 or more, with the proviso that g+j+k+q is 5 or less; h represents an integer of 1 or more, and l and m each independently represents 0 or an integer of 1 or more, with the proviso that h+l+m is 4 or less; i represents an integer of 1 or more, and n and o each independently represents 0 or an integer of 1 or more, with the proviso that i+n+o is 4 or less; and X represents an aliphatic cyclic group.

Furthermore, a third aspect of the present invention is a method of forming a resist pattern, including: applying a positive resist composition of the second aspect onto a substrate to form a resist film on the substrate; conducting exposure of the resist film; and developing the resist film to form a resist pattern.

In the present claims and description, the term "alkyl group" refers to a monovalent saturated hydrocarbon group, unless otherwise specified.

The term "aliphatic" is a relative concept used in relation to the term "aromatic", and defines a group or compound that has no aromaticity. Further, the term "aliphatic cyclic group" refers to a monocyclic group or polycyclic group that has no aromaticity.

The term "exposure" is used as a general concept that includes irradiation with any form of radiation.

dissociable, dissolution inhibiting groups dissociate upon generation of acid from the acid generator component (B) by exposure, and the entire compound (A1) changes from alkali-insoluble to alkali soluble.

Polyhydric Phenol Compound (I)

In general formula (I), $R^{11}$ to $R^{17}$ each independently represents a linear, branched or cyclic alkyl group of 1 to 10 carbon atoms or an aromatic hydrocarbon group.

As the alkyl group, a linear or branched lower alkyl group of 1 to 5 carbons or a cyclic group of 5 or 6 carbon atoms is preferable. Specific examples include linear or branched lower alkyl groups such as a methyl group, ethyl group, propyl group, isopropyl group, n-butyl group, isobutyl group, tert-butyl group, pentyl group, isopentyl group and neopentyl group. Among these, a methyl group is particularly desirable. Specific examples of cyclic alkyl groups include a cyclohexyl group and cyclopentyl group.

The aromatic hydrocarbon preferably has 6 to 15 carbon atoms, and examples include a phenyl group, a tolyl group, a xylyl group, a mesityl group, a phenethyl group and a naphtyl group.

The alkyl group or aromatic hydrocarbon group may have a hetero atom such as an oxygen atom, a nitrogen atom or a sulfur atom in the structure thereof.

g and j each independently represents an integer of 1 or more, preferably an integer of 1 to 2, and k and q each independently represents 0 or an integer of 1 or more, preferably 0 or an integer of 1 or more and not exceeding 2, with the proviso that g+j+k+q is 5 or less.

h represents an integer of 1 or more, preferably an integer of 1 to 2, and l and m each independently represents 0 or an integer of 1 or more, preferably 0 or an integer of 1 or more and not exceeding 2, with the proviso that h+l+m is 4 or less.

i represents an integer of 1 or more, preferably an integer of 1 to 2, and n and o each independently represents 0 or an integer of 1 or more, preferably 0 or an integer of 1 or more and not exceeding 2, with the proviso that i+n+o is 4 or less.

X represents an aliphatic cyclic group.

The aliphatic cyclic group may or may not have a substituent. Examples of the substituent include lower alkyl groups of 1 to 5 carbon atoms, a fluorine atom, fluorinated lower alkyl groups of 1 to 5 carbon atoms and an oxygen atom (=O).

The basic ring of the aliphatic cyclic group exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the hydrocarbon group is preferably a polycyclic group.

As such aliphatic cyclic groups, groups in which two hydrogen atoms have been removed from a polycycloalkane such as a bicycloalkane, tricycloalkane or tetracycloalkane may be exemplified. Specific examples include groups in which two hydrogen atoms have been removed from a monocycloalkane such as cyclopentane and cyclohexane; and groups in which two hydrogen atoms have been removed from a polycycloalkane such as adamantane, norbornane, isobornane, tricyclodecane or tetracyclododecane. These groups may have some or all of the hydrogen atoms substituted with substituents (e.g., lower alkyl groups, fluorine atoms or fluorinated lower alkyl groups).

Of these, aliphatic cyclic groups of 4 to 15 carbon atoms are preferable, and a group in which two hydrogen atoms have been removed from adamantane is preferable, and a group in which two hydrogen atoms have been removed from the 1- and 3-positions of an adamantane is particularly desirable.

As the polyhydric phenol compound (I), compounds represented by general formula (I-1) are preferable, as they exhibit excellent effects of the present invention.

[Chemical Formula 3]

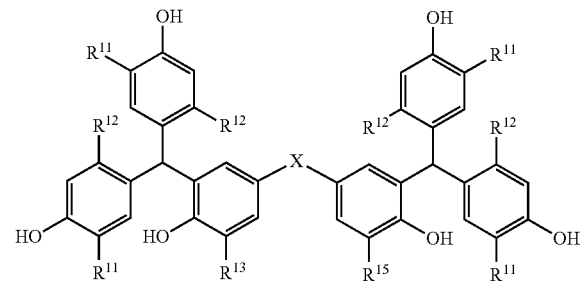

(I-1)

wherein each of $R^{11}$, $R^{12}$, $R^{13}$ and $R^{15}$ each independently represents an alkyl group of 1 to 10 carbon atoms or aromatic hydrocarbon group which may contain a hetero atom in the structure thereof; and X represents an aliphatic cyclic group.

In formula (I-1) above, $R^{11}$, $R^{12}$, $R^{13}$, $R^{15}$ and X are the same as $R^{11}$, $R^{12}$, $R^{13}$, $R^{15}$ and X defined for formula (I) above.

In the present invention, it is necessary that the polyhydric phenol compound (I) have a molecular weight of 300 to 2,500, preferably 450 to 1,500, and more preferably 500 to 1,200. When the molecular weight is within the above-mentioned range, roughness is reduced, and a pattern exhibiting an excellent resolution can be formed. Further, the profile of the resist pattern becomes satisfactory.

Further, with respect to the polyhydric phenol compound (I), it is preferable that the dispersion degree of the molecular weight (Mw/Mn) be 1.5 or less, as the effects of the present invention are improved. The reason for this is presumed to be because, when the polyhydric phenol compound (I) has a narrow molecular weight distribution in which the dispersion degree is 1.5 or less, even if the compound (A1) contains a plurality of polyhydric phenol compounds (A1) with differing quantities of phenolic hydroxyl groups protected with acid dissociable, dissolution inhibiting groups (different protection numbers), the alkali solubility of each of these compounds will be comparatively uniform. Smaller dispersion degree values are preferred, and the dispersion degree is more preferably 1.4 or less, most preferably 1.3 or less.

Dispersion degree is usually used for polydisperse compounds such as polymers, but even for monodisperse compounds, the existence of impurities such as production by-products or residual starting materials can result in the appearance of an apparent molecular weight distribution when analysis is conducted using gel permeation chromatography (GPC) or the like. In other words, in the case of a monodisperse compound, a dispersion degree of 1 indicates a purity degree of 100%, and increasingly large dispersion degrees indicate large quantities of impurities. In the present invention, the dispersion degree is calculated for compounds that exhibit the above type of apparent molecular weight distribution by measuring the weight average molecular weight (Mw) and the number average molecular weight (Mn) using a typical method used for the measurement of these Mw and Mn values for a polymer, such as a GPC method, and then determining the Mw/Mn ratio.

The dispersion degree can be adjusted either by removing reaction by-products and impurities following synthesis of the polyhydric phenol compound (I) which is the targeted product, or by using conventional methods such as molecular weight fractionation treatments to remove the unnecessary fractions having undesired molecular weight.

Further, it is necessary that the polyhydric phenol compound (I) be a material capable of forming an amorphous (non-crystalline) film using a spin-coating method.

In this description, an amorphous film refers to an optically transparent film that does not crystallize.

Spin-coating is one of the most commonly used techniques for forming thin films, and an evaluation as to whether or not a polyhydric phenol compound is capable of forming an amorphous film using spin-coating is determined on the basis of whether or not a film formed by spin-coating onto an 8-inch silicon wafer is transparent across the entire film surface.

More specifically, evaluation can be conducted, for example, in the manner described as follows. First, the polyhydric phenol material is added to a solvent typically used as a resist solvent such as a mixed solvent of ethyl lactate and propylene glycol monoethyl ether acetate in a ratio (weight ratio) of 40/60 (hereafter this solvent is abbreviated as EM), in sufficient quantity to generate a solution with a concentration of 14% by weight, and dissolution is performed by ultrasound treatment (dissolution treatment) using an ultrasound cleaning apparatus. Then, the resultant solution is spin-coated onto a wafer at 1,500 rpm and optionally subjected to drying and baking (PAB: Post Applied Bake) at 110° C. for 90 seconds. A visual assessment as to whether the formed film is transparent is then used to confirm whether or not an amorphous film has been formed. A non-transparent, cloudy film is not an amorphous film.

In the present invention, the polyhydric phenol compound (I) preferably exhibits favorable stability for the amorphous film formed in the manner described above, and compounds for which the amorphous state is retained even after being allowed to stand for 2 weeks at room temperature following the above PAB treatment are particularly desirable.

The polyhydric phenol compound (I) can be synthesized, for example, by dissolving a bissalicylaldehyde derivative in which 2 salicylaldehydes (which may have a substituent) are bonded through an aliphatic cyclic group in an organic solvent with about 4 equivalents of a phenol derivative per 1 equivalent of the bissalicylaldehyde derivative, followed by reacting under acidic conditions.

The compound (A1) is a polyhydric phenol compound (I) in which some or all of the hydrogen atoms of the phenolic hydroxyl groups are substituted with acid dissociable, dissolution inhibiting groups.

The acid dissociable, dissolution inhibiting groups are groups which exhibits alkali dissolution inhibiting property to render the entire compound (A1) alkali-insoluble prior to dissolution, and changes the entire compound (A1) alkali-soluble following dissolution. Therefore, when the compound (A1) constitutes a positive resist composition with the acid generator component (B), the acid dissociable, dissolution inhibiting groups dissociate upon generation of acid from the component (B) by exposure, and the entire compound (A1) changes from alkali-insoluble to alkali soluble.

There are no particular restrictions on the acid dissociable, dissolution inhibiting groups, and any group can be appropriately selected from amongst the various acid dissociable, dissolution inhibiting groups proposed for use within the hydroxystyrene-based resins and (meth)acrylate-based resins and the like used within conventional KrF or ArF chemically amplified resist compositions. The term "(meth)acrylate" is a generic term that includes either or both of the acrylate and the methacrylate. Specific examples include tertiary alkyl groups, tertiary alkyloxycarbonyl groups, tertiary alkoxycarbonylalkyl groups, alkoxyalkyl groups and cyclic ether groups.

Specific examples of suitable tertiary alkyl groups include chain-like tertiary alkyl groups such as a tert-butyl group and a tert-amyl group, and tertiary alkyl groups that include an aliphatic polycyclic group such as a 2-methyl-2-adamantyl group or a 2-ethyl-2-adamantyl group.

As the tertiary alkyl groups of the tertiary alkyloxycarbonyl groups, the same as those exemplified above can be mentioned. Specific examples of tertiary alkyloxycarbonyl groups include a tert-butyloxycarbonyl group and tert-amyloxycarbonyl group.

Specific examples of suitable cyclic ether groups include a tetrahydropyranyl group and tetrahydrofuranyl group.

In the present invention, especially in terms of improving the effects of the present invention, the compound (A1) preferably has acid dissociable, dissolution inhibiting groups which are at least one member selected from the group consisting of alkoxycarbonylalkyl groups represented by general formula (p1) shown below and alkoxyalkyl groups represented by general formula (p2) shown below.

[Chemical Formula 4]

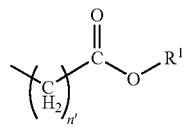

(p1)

-continued

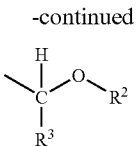

(p2)

wherein $R^1$ and $R^2$ each independently represents a linear, branched or cyclic alkyl groups which may contain a hetero atom in the structure thereof; $R^3$ represents a hydrogen atom or a lower alkyl group; and n' represents an integer of 1 to 3.

In general formula (p1) above, n' represents an integer of 1 to 3, and is preferably 1.

$R^1$ represents a linear, branched or cyclic alkyl group which may contain a hetero atom in the structure thereof. In other words, the alkyl group as $R^1$ may have some or all of the hydrogen atoms substituted with hetero atom-containing groups (which includes hetero atoms themselves), or some of the carbon atoms of the alkyl group may be substituted with hetero atoms.

Examples of hetero atoms include an oxygen atom, a sulfur atom, a nitrogen atom and a fluorine atom.

The hetero atom-containing groups may be the hetero atoms themselves. Alternatively, the hetero atom-containing groups may be groups consisting of hetero atoms and carbon atoms and/or hydrogen atoms, such as alkoxy groups.

Examples of alkyl groups in which some or all of the hydrogen atoms are substituted with hetero atom-containing groups include lower fluorinated alkyl groups of 1 to 5 carbon atoms in which some or all of the hydrogen atoms substituted with fluorine atoms; groups in which 2 hydrogen atoms bonded to a carbon atom are substituted with 1 oxygen atom (i.e., groups having a carbonyl group (C=O)); and groups in which 2 hydrogen atoms bonded to a carbon atom are substituted with 1 sulfur atom (i.e., groups having a thiocarbonyl group (C=S)).

Examples of groups in which some of the carbon atoms of the alkyl group are substituted with hetero atoms include groups in which the carbon atoms are substituted with nitrogen atoms (e.g., groups having a branched or cyclic alkyl group including —CH$_2$— which is substituted with —NH—); and groups in which the carbon atoms are substituted with oxygen atoms (e.g., groups having a branched or cyclic alkyl group including —CH$_2$— which is substituted with —O—).

The linear alkyl group as $R^1$ preferably has 1 to 5 carbon atoms, and specific examples include a methyl group, ethyl group, n-propyl group, n-butyl group, isobutyl group and n-pentyl group. Of these, a methyl group or ethyl group is particularly desirable.

The branched alkyl group as $R^1$ preferably has 4 to 10 carbon atoms, and more preferably 4 to 8 carbon atoms. Specific examples include an isobutyl group, tert-butyl group, isopentyl group, neopentyl group and tert-pentyl group. Of these, tert-butyl group is particularly desirable.

The cyclic group as $R^1$ preferably has 3 to 20 carbon atoms, more preferably 4 to 14 carbon atoms, and most preferably 5 to 12 carbon atoms.

The structure of the basic ring (the basic ring exclusive of substituents) of the cyclic alkyl group may be monocyclic or polycyclic, although polycyclic is preferable in terms of improving the effects of the present invention. Further, the basic ring may be a hydrocarbon ring constituted from only carbon and hydrogen, or a hetero ring in which some of the carbon atoms constituting the ring of the hydrocarbon ring are substituted with hetero atoms. In the present invention, it is particularly desirable that the basic ring be a hydrocarbon ring. Examples of hydrocarbon rings include monocycloalkanes, bicycloalkanes, tricycloalkanes and tetracycloalkanes. Specific examples include monocycloalkanes such as cyclopentane and cyclohexane, and polycycloalkanes such as adamantane, norbornane, isobornane, tricyclodecane and tetracyclododecane. Of these, adamantane, norbornane tricyclodecane and tetracyclododecane are preferable, and adamantane is particularly desirable.

These basic rings may or may not have a substituent on the ring. Examples of such substituents include lower alkyl groups, fluorine atom, fluorinated lower alkyl groups and oxygen atom (=O). Examples of lower alkyl groups include linear or branched alkyl groups of 1 to 5 carbon atoms such as a methyl group and ethyl group. The fluorinated lower alkyl groups are lower alkyl groups being substituted with fluorine atoms, and the same as those mentioned above can be exemplified as the lower alkyl groups for the fluorinated lower alkyl groups. When the basic ring has a substituent, the number of substituents is preferably 1 to 3, and more preferably 1. Here, the expression "have a substituent" means that the hydrogen atom(s) bonded to the carbon atoms constituting the basic ring is replaced with the substituent.

Examples of cyclic alkyl group as $R^1$ include groups in which one hydrogen atom has been removed from the basic ring. With respect to $R^1$, it is preferable that the carbon atom having bonded thereto an oxygen atom adjacent to $R^1$ be one of the carbon atoms constituting the basic ring. In terms of improving the effects of the present invention, it is particularly desirable that the carbon atom having bonded thereto an oxygen atom adjacent to $R^1$ be a tertiary carbon atom having a substituent such as a lower alkyl group.

As the acid dissociable, dissolution inhibiting group having the cyclic alkyl group as $R^1$, the groups represented by following formulas can be exemplified.

[Chemical Formula 5]

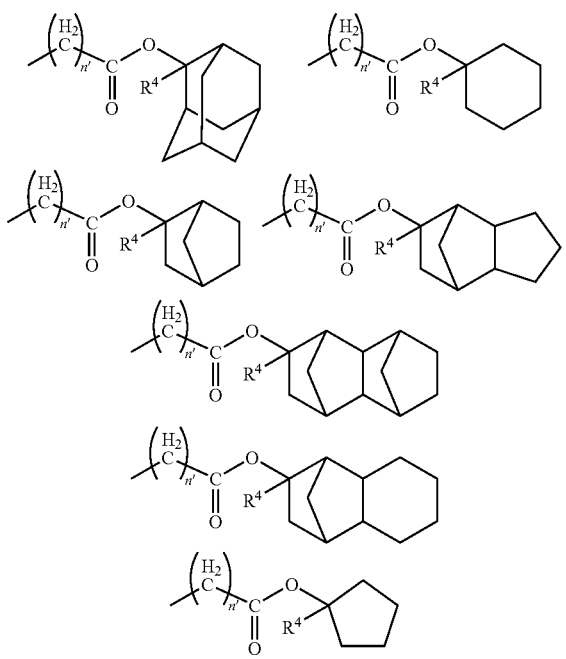

wherein $R^4$ is a lower alkyl group, and n' is as defined above.

Of these, those represented by general formula shown below are preferable.

[Chemical Formula 6]

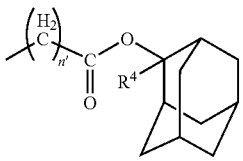

wherein $R^4$ is a lower alkyl group, and n' is as defined above.

The lower alkyl group as $R^4$ is an alkyl group of 1 to 5 carbon atoms, and specific examples include linear or branched lower alkyl groups such as a methyl group, ethyl group, propyl group, isopropyl group, n-butyl group, isobutyl group, tert-butyl group, pentyl group, isopentyl group and neopentyl group. In terms of industrial availability, $R^4$ is preferably a methyl group or ethyl group, and a methyl group is particularly desirable.

In general formula (p2) shown above, as $R^2$, the same as those mentioned above for $R^1$ can be exemplified. Among these, it is preferable that $R^2$ is a linear alkyl group or a cyclic alkyl group.

$R^3$ is a hydrogen atom or a lower alkyl group. The lower alkyl group as $R^3$ is an alkyl group of 1 to 5 carbon atoms, and specific examples include linear or branched lower alkyl groups such as a methyl group, ethyl group, propyl group, isopropyl group, n-butyl group, isobutyl group, tert-butyl group, pentyl group, isopentyl group and neopentyl group. In terms of industrial availability, $R^3$ is preferably a hydrogen atom or a methyl group, and more preferably a hydrogen atom.

Examples of groups represented by general formula (p2) in which $R^2$ is a linear alkyl group include a 1-ethoxyethyl group, 1-ethoxymethyl group, 1-methoxyethyl group, 1-methoxymethyl group, 1-methoxypropyl group, 1-ethoxypropyl group, 1-n-butoxyethyl group, 1-pentafluoroethoxyethyl group, 1-trifluoromethoxyethyl group and 1-trifluoromethoxymethyl group.

Examples of groups represented by general formula (p2) in which $R^2$ is a cyclic alkyl group include those represented by formulas shown below.

[Chemical Formula 7]

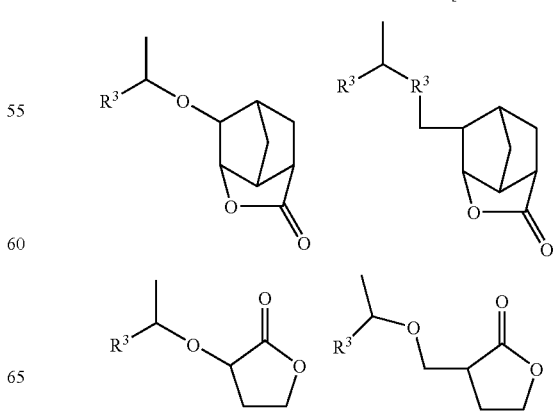

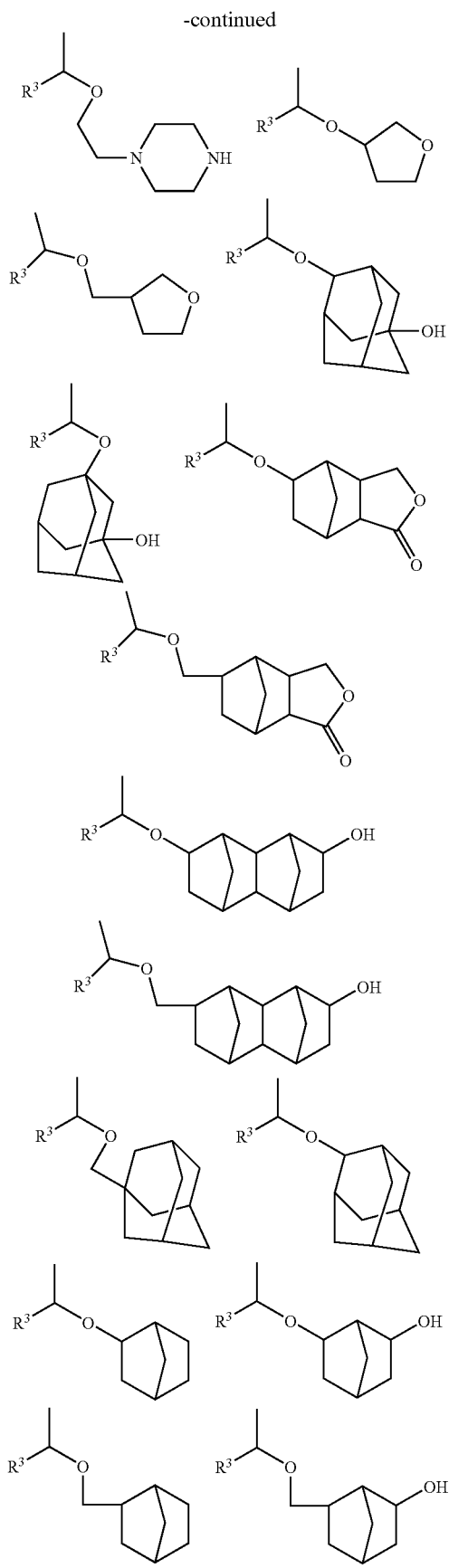

wherein $R^3$ is as defined above.

As groups represented by general formula (p2), compounds represented by general formula shown below are particularly desirable.

[Chemical Formula 8]

wherein $R^3$ is as defined above; $n''$ represents 0 or an integer of 1 to 2; and W represents two hydrogen atoms or one oxygen atom.

$n''$ is most preferably 0 or 1.

The bonding position of —CH($R^3$)—O—($CH^2$)$_{n''}$— to the adamantyl group is not particularly limited, but is preferably the 1- or 2-position of the adamantyl group.

With respect to the compound (A1), the protection ratio of the phenolic hydroxyl groups within the compound (A1), i.e., the percentage (mol %) of "the phenolic hydroxyl groups protected with acid dissociable, dissolution inhibiting groups", based on "the total of the phenolic hydroxyl groups protected with acid dissociable, dissolution inhibiting groups and the phenolic hydroxyl groups which are not protected with acid dissociable, dissolution inhibiting groups" can be appropriately determined depending on the structure of the polyhydric phenol compound (I), the number of phenolic hydroxyl groups, and the desired lithography properties. For example, in terms of resolution and reducing roughness, the protection ratio is preferably 5 to 50 mol %, more preferably 7 to 45 mol %, and still more preferably 15 to 45 mol %.

The compound (A1) can be produced, for example, by substituting some or all of the hydrogen atoms of the phenolic hydroxyl groups of the polyhydric phenol compound (I) with acid dissociable, dissolution inhibiting groups by a conventional method.

<<Positive Resist Composition>>

The positive resist composition according to the second aspect of the present invention includes a base component (A) (hereafter referred to as "component (A)") which has acid dissociable dissolution inhibiting groups and exhibits increased alkali solubility under action of acid, and an acid generator component (B) (hereafter, referred to as "component (B)") which generates acid upon exposure.

When the acid generated from the component (B) upon exposure acts on the component (A), the acid dissociable, dissolution inhibiting groups are dissociated, thereby changing the entire component (A) from alkali insoluble to alkali soluble. Therefore, in the formation of a resist pattern, when the positive resist composition is subjected to selective exposure, the exposed area becomes soluble in an alkali, while the unexposed area remains alkali-insoluble, and hence a resist pattern can be formed by alkali developing.

In the positive resist composition according to the second aspect of the present invention, it is necessary that the component (A) includes the compound (A1) according to the first aspect of the present invention.

As the compound (A1), one type of compound may be used, or two or more types of compounds may be used in combination.

In the component (A), the amount of the compound (A1) is preferably more than 40% by weight, more preferably more than 50% by weight, still more preferably more than 80% by weight, and most preferably 100% by weight.

The amount of the compound (A1) within the component (A) can be determined by reversed phase chromatography or the like.

The component (A) may further include any desired resin component proposed as a base component for chemically amplified resists, as long as the effects of the present invention are not impaired.

Examples of such resin components include those which have been proposed as base resins for a conventional chemically amplified positive resist composition for KrF or ArF. The resin component can be appropriately selected depending on the type of exposure source for formation of a resist pattern.

In the positive resist composition according to the second aspect of the present invention, the amount of the component (A) can be adjusted depending on the film thickness of the resist to be formed.

As the component (B), there is no particular limitation, and any of the known acid generators used in conventional chemically amplified resist compositions can be used. Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

Examples of onium salt-based acid generators include compounds represented by general formula (b-1) or (b-2) shown below.

[Chemical Formula 9]

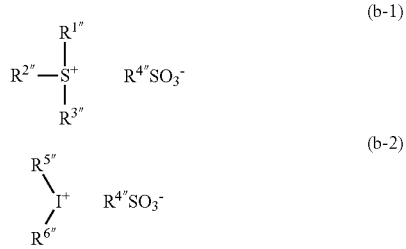

wherein $R^{1\prime\prime}$ to $R^{3\prime\prime}$, $R^{5\prime\prime}$ and $R^{6\prime\prime}$ each independently represents an aryl group or alkyl group; and $R^{4\prime\prime}$ represents a linear, branched or cyclic alkyl group or fluorinated alkyl group, with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ each independently represents an aryl group or an alkyl group. Among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not specifically limited. For example, an aryl group having 6 to 20 carbon atoms may be used in which some or all of the hydrogen atoms of the aryl group may or may not be substituted with alkyl groups, alkoxy groups or halogen atoms. The aryl group is preferably an aryl group having 6 to 10 carbon atoms because it can be synthesized at a low cost. Specific examples thereof include a phenyl group and naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, and most preferably a methoxy group or an ethoxy group.

The halogen atom, with which hydrogen atoms of the aryl group may be substituted, is preferably a fluorine atom.

The alkyl group for $R^{1\prime\prime}$ to $R^{3\prime\prime}$ is not specifically limited and includes, for example, a linear, branched or cyclic alkyl group having 1 to 10 carbon atoms. In consideration of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is particularly desirable that all of $R^{1\prime\prime}$ to $R^{3\prime\prime}$ are phenyl groups.

$R^{4\prime\prime}$ represents a linear, branched or cyclic alkyl or fluorinated alkyl group.

The linear alkyl group preferably has 1 to 10 carbon atoms, more preferably 1 to 8 carbon atoms, and most preferably 1 to 4 carbon atoms.

The cyclic alkyl group is preferably a cyclic group, as described for $R^{1\prime\prime}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (ratio of fluorine atoms within the alkyl group) is preferably from 10 to 100%, more preferably from 50 to 100%, and it is particularly desirable that all hydrogen atoms are substituted with fluorine atoms because the acid strength increases.

$R^{4\prime\prime}$ is most preferably a linear or cyclic alkyl group or fluorinated alkyl group.

In formula (b-2), $R^{5\prime\prime}$ and $R^{6\prime\prime}$ each independently represents an aryl group or alkyl group. At least one of $R^{5\prime\prime}$ and $R^{6\prime\prime}$ represents an aryl group. It is preferable that both of $R^{5\prime\prime}$ and $R^{6\prime\prime}$ represents an aryl group.

As the aryl group for $R^{5\prime\prime\prime}$ and $R^{6\prime\prime\prime}$, the same as the aryl groups for $R^{1\prime\prime\prime}$ to $R^{3\prime\prime\prime}$ can be exemplified.

As the alkyl group for $R^{5\prime\prime\prime}$ and $R^{6\prime\prime\prime}$, the same as the alkyl groups for $R^{1\prime\prime\prime}$ to $R^{3\prime\prime\prime}$ can be exemplified.

It is particularly desirable that both of $R^{5\prime\prime\prime}$ and $R^{6\prime\prime\prime}$ represents a phenyl group.

As $R^{4\prime\prime\prime}$ in formula (b-2), the same as those mentioned above for $R^{4\prime\prime\prime}$ in formula (b-1) can be exemplified.

Specific examples of suitable onium salt-based acid generators include diphenyliodonium trifluoromethanesulfonate or nonafluorobutanesulfonate, bis(4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl)diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, and diphenyl(1-(4-methoxy)naphthyl)sulfonium trifluoromethanesulfonate, heptafluoropropanesulfonate or nonafluorobutanesulfonate. It is also possible to use onium salts in which the anion moiety of these onium salts are replaced by methanesulfonate, n-propanesulfonate, n-butanesulfonate, or n-octanesulfonate.

Further, acid generators in which the anion moiety in general formula (b-1) or (b-2) is replaced with an anion moiety represented by general formula (b-3) or (b-4) shown below (the cation moiety is the same as (b-1) or (b-2)) may be used.

[Chemical Formula 10]

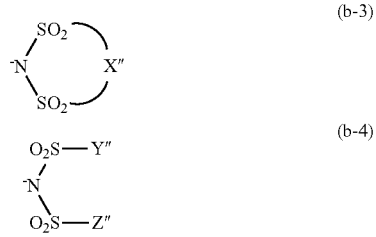

wherein X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Y" and Z" each independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group of X" or those of the alkyl group of Y" and Z" within the range of the number of carbon atoms, the more the solubility in a resist solvent becomes better.

Further, in the alkylene group of X" or the alkyl group of Y" and Z", it is preferable that the number of hydrogen atoms substituted with a fluorine atom is as large as possible, as the acid strength increases, and the transparency to high energy radiation of 200 nm or less or electron beam is improved. The fluorination ratio the alkylene group or alkyl group is preferably from 70 to 100%, more preferably from 90 to 100%, and it is particularly desirable that the alkylene group or alkyl group a perfluoroalkylene or perfluoroalkyl group in which all hydrogen atoms are substituted with fluorine atoms.

In the present invention, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

[Chemical Formula 11]

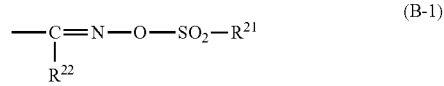

wherein $R^{21}$ and $R^{22}$ each independently represents an organic group.

In the invention, the 'organic group' refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{21}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that some or all of the hydrogen atoms of the alkyl group or the aryl group are replaced with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and the fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted by halogen atoms.

As $R^{21}$, an alkyl group of 1 to 4 carbon atoms which has no substituent or a fluorinated alkyl group of 1 to 4 carbon atoms is particularly desirable.

As the organic group for $R^{22}$, a linear, branched, or cyclic alkyl group, aryl group, or cyano group is preferable. Examples of the alkyl group and the aryl group for $R^{22}$ are the same as those of the alkyl group and the aryl group for $R^{21}$.

As $R^{22}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 12]

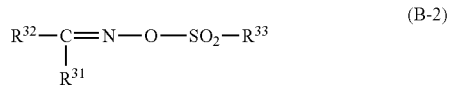

wherein $R^{31}$ represents a cyano group, an alkyl group having no substituent or a halogenated alkyl group; $R^{32}$ represents an aryl group; and $R^{33}$ represents an alkyl group having no substituent or a halogenated alkyl group.

[Chemical Formula 13]

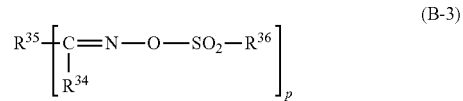

wherein $R^{34}$ represents a cyano group, an alkyl group having no substituent or a halogenated alkyl group; $R^{35}$ represents a divalent or trivalent aromatic hydrocarbon group; $R^{36}$ represents an alkyl group having no substituent or a halogenated alkyl group; and p represents 2 or 3.

In general formula (B-2), the alkyl group having no substituent or the halogenated alkyl group for $R^{31}$ preferably has 1 to 10 carbon atoms, more preferably 1 to 8 carbon atoms, and most preferably 1 to 6 carbon atoms.

As for the $R^{31}$, a halogenated alkyl group is preferable, and a fluorinated alkyl group is more preferable.

The fluorinated alkyl group for $R^{31}$ preferably has 50% or more of the hydrogen atoms thereof fluorinated, more preferably 70% or more, and still more preferably 90% or more.

Examples of the aryl group for $R^{32}$ include groups in which one hydrogen atom has been removed from an aromatic hydrocarbon ring, such as a phenyl group, a biphenyl group, a fluorenyl group, a naphthyl group, an anthracyl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{32}$ may have a substituent such as an alkyl group of 1 to 10 carbon atoms, a halogenated alkyl group, and alkoxy group. The alkyl group and the halogenated alkyl group serving as the substituent preferably has 1 to 8 carbon atoms, and more preferably 1 to 4 carbon atoms. The halogenated alkyl group thereof is preferably a fluorinated alkyl group.

The alkyl group having no substituent or the halogenated alkyl group for $R^{33}$ preferably has 1 to 10 carbon atoms, more preferably 1 to 8 carbon atoms, most preferably 1 to 6 carbon atoms.

As $R^{33}$, a halogenated alkyl group is preferable, and a partially or completely fluorinated alkyl group is more preferable.

In terms of enhancing the strength of the acid generated, the fluorinated alkyl group for $R^{33}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{34}$ are the same as the alkyl group having no substituent and the halogenated alkyl group for $R^{31}$.

Examples of the divalent or trivalent aromatic hydrocarbon group for $R^{35}$ include groups in which one or two hydrocarbon atoms have been removed from the aryl group for $R^{32}$.

As the alkyl group having no substituent or the halogenated alkyl group for $R^{36}$, the same one as the alkyl group having no substituent or the halogenated alkyl group for $R^{33}$ can be used.

p is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, compounds represented by chemical formulas shown below can be exemplified.

[Chemical Formula 14]
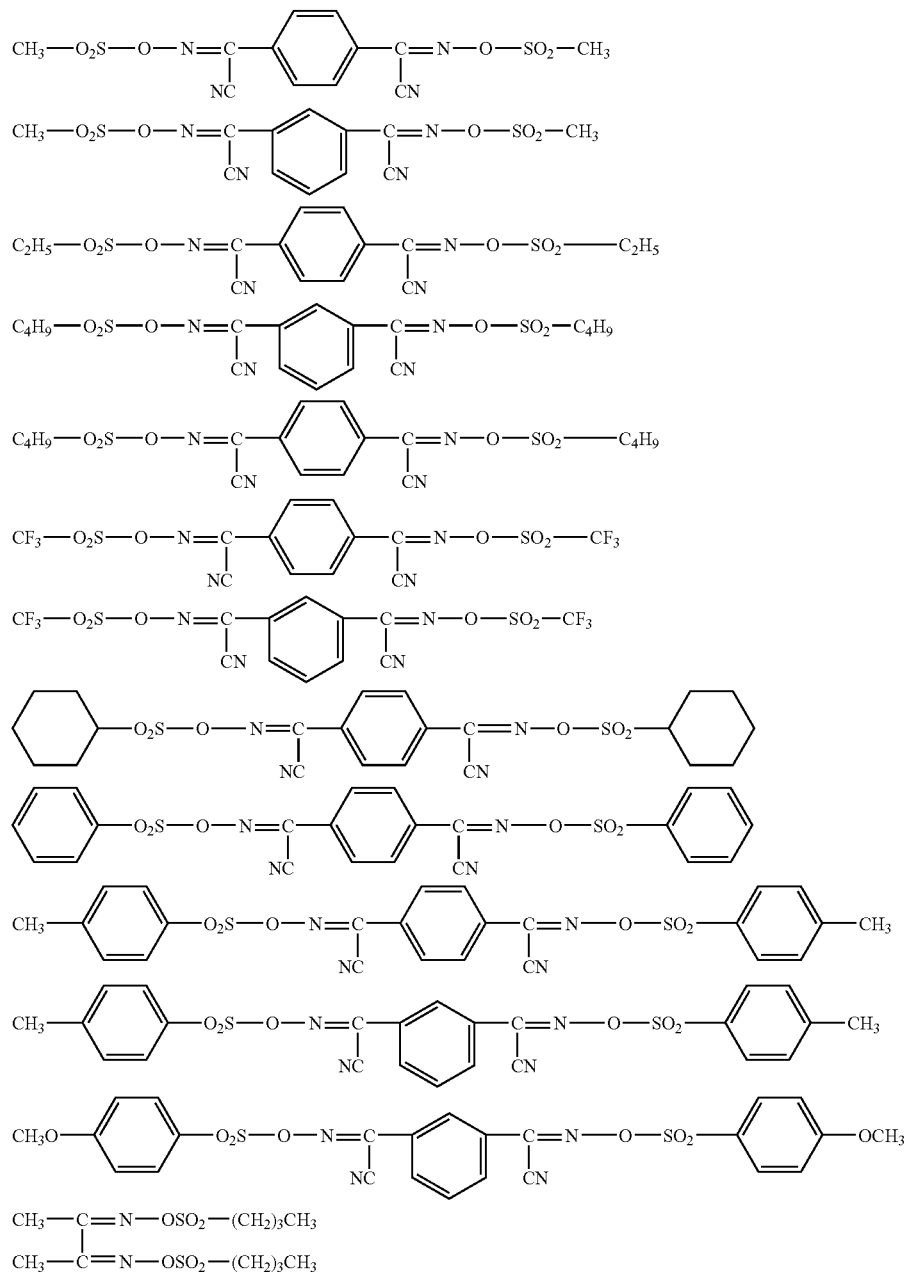
Furthermore, preferable compounds among the compounds represented by general formula (B-2) or (B-3) shown above are exemplified below.
[Chemical Formula 15]
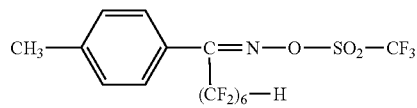
-continued
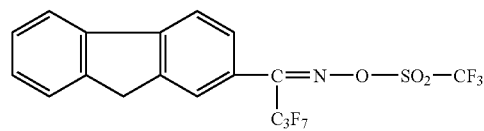
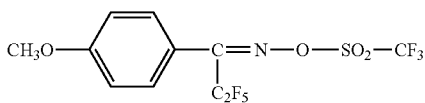

-continued
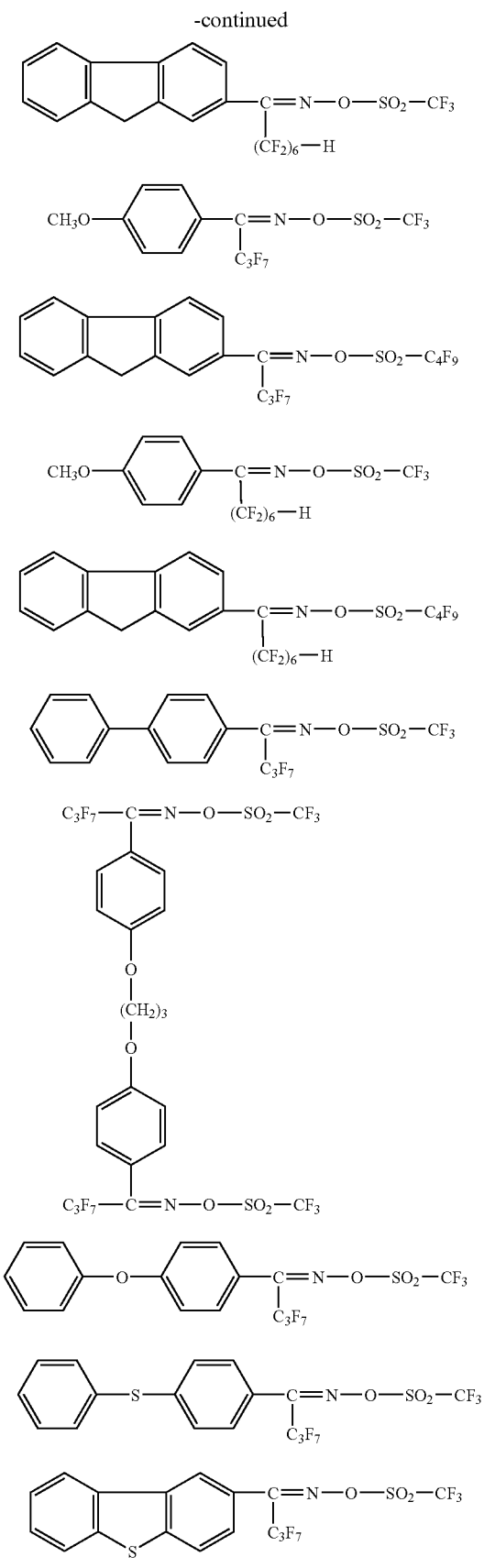
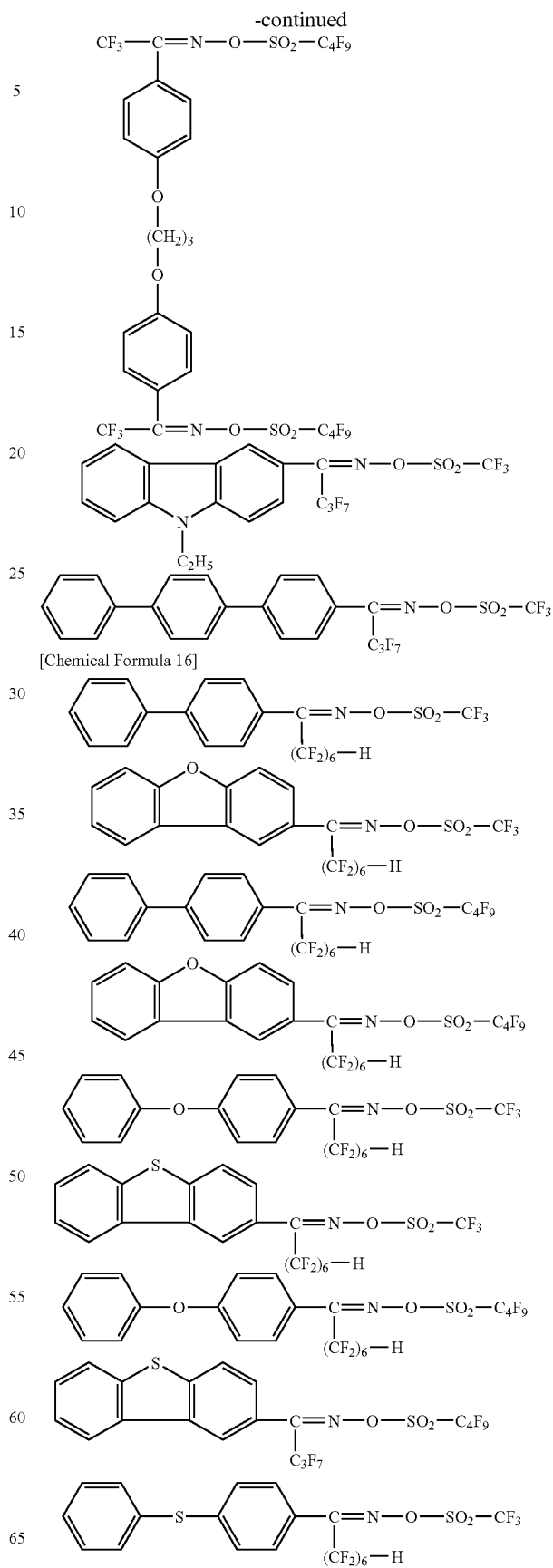

-continued

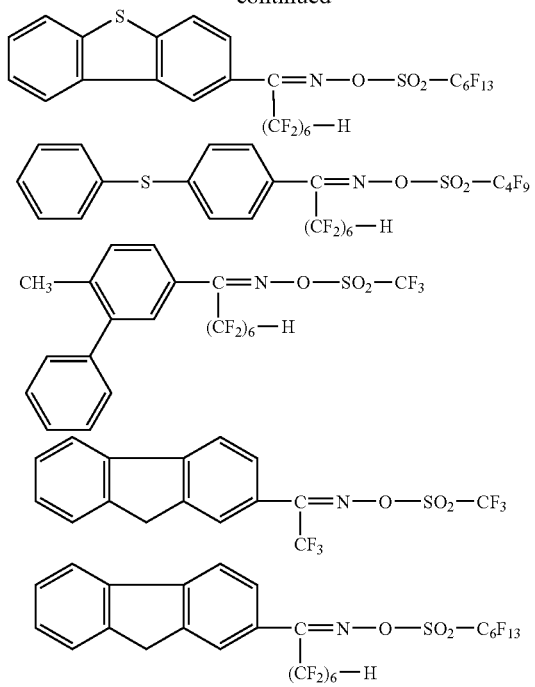

Among the above-exemplified compounds, the following 3 compounds are preferable.

[Chemical Formula 17]

C$_4$H$_9$—O$_2$S—O—N=C—⟨phenyl⟩—C=N—O—SO$_2$—C$_4$H$_9$
         |                    |
         CN                   CN

[Chemical Formula 18]

CH$_3$—C=N—OSO$_2$—(CH$_2$)$_3$CH$_3$
CH$_3$—C=N—OSO$_2$—(CH$_2$)$_3$CH$_3$

[Chemical Formula 19]

⟨fluorene⟩—C=N—O—SO$_2$—C$_4$F$_9$
           |
           (CF$_2$)$_6$—H

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Furthermore, specific examples of poly(bis-sulfonyl)diazomethanes include those having the structures shown below, such as 1,3-bis(phenylsulfonyldiazomethylsulfonylpropane (A=3), 1,4-bis(phenylsulfonyldiazomethylsulfonylbutane (A=4), 1,6-bis(phenylsulfonyldiazomethylsulfonyl)hexane (A=6), 1,10-bis(phenylsulfonyldiazomethylsulfonyl)decane (A=10), 1,2-bis(cyclohexylsulfonyldiazomethylsulfonyl)ethane (B=2), 1,3-bis(cyclohexylsulfonyldiazomethylsulfonyl)propane (B=3), 1,6-bis(cyclohexylsulfonyldiaz- omethylsulfonyl)hexane (B=6), and 1,10-bis(cyclohexylsulfonyldiazomethylsulfonyl)decane (B=10).

[Chemical Formula 20]

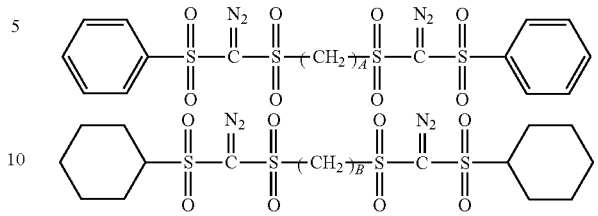

In the present invention, as the component (B), it is preferable to use an onium salt having a fluorinated alkylsulfonate ion or an alkylsulfonate ion as the anion moiety.

As the component (B), one type of compound may be used, or two or more types of compounds may be used in combination.

The amount of the component (B) is 0.5 to 30 parts by weight, and preferably 1 to 10 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

[Optional Component]

In the positive resist composition of the present invention, for improving the resist pattern shape and the post exposure stability of the latent image formed by the pattern-wise exposure of the resist layer, it is preferable to add a nitrogen-containing organic compound (D) (hereafter referred to as the component (D)).

A multitude of these components (D) have already been proposed, and any of these known compounds may be used. Specific examples of these aliphatic amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, secondary aliphatic amines and tertiary aliphatic amines are preferable, trialkyl amines of 5 to 10 carbon atoms are more preferable, and tri-n-octylamine is particularly desirable. Among alkyl alcohol amines, triethanolamine and triisopropanolamine are preferable.

These compounds can be used either alone, or in combinations of two or more different compounds.

The component (D) is typically used in an amount within a range from 0.01 to 5.0 parts by weight, relative to 100 parts by weight of the component (A).

Furthermore, in the positive resist composition of the present invention, for preventing any deterioration in sensitivity caused by the addition of the above component (D), and improving the resist pattern shape and the post exposure stability of the latent image formed by the pattern-wise exposure of the resist layer, an organic carboxylic acid, or a phosphorus oxo acid or derivative thereof (E) (hereafter referred to as the component (E)) can also be added as another optional component.

The component (D) and the component (E) can be used in combination, or either one can also be used alone.

Examples of suitable organic carboxylic acids include malonic acid, citric acid, malic acid, succinic acid, benzoic acid, and salicylic acid.

Examples of suitable phosphorus oxo acids or derivatives thereof include phosphoric acid or derivatives thereof such as esters, including phosphoric acid, di-n-butyl phosphate and diphenyl phosphate; phosphonic acid or derivatives thereof such as esters, including phosphonic acid, dimethyl phosphonate, di-n-butyl phosphonate, phenylphosphonic acid, diphenyl phosphonate, and dibenzyl phosphonate; and phosphinic acid or derivatives thereof such as esters, including phosphinic acid and phenylphosphinic acid, and of these, phosphonic acid is particularly desirable.

The component (E) is typically used in an amount within a range from 0.01 to 5.0 parts by weight, relative to 100 parts by weight of the component (A).

If desired, other miscible additives can also be added to the positive resist composition according to the second aspect of the present invention. Examples of such miscible additives include additive resins for improving the performance of the resist film, surfactants for improving the applicability, dissolution inhibitors, plasticizers, stabilizers, colorants, halation prevention agents, and dyes.

The positive resist composition according to the second aspect of the present invention can be prepared by dissolving a component (A), a component (B) and optionally other components in an organic solvent (S).

The organic solvent (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl isoamyl ketone, and 2-heptanone; polyhydric alcohols and derivatives thereof, such as ethylene glycol, ethylene glycol monoacetate, diethylene glycol, diethylene glycol monoacetate, propylene glycol, propylene glycol monoacetate, dipropylene glycol, and monomethylether, monoethylether, monopropylether, monobutylether or monophenylether of any of these polyhydric alcohols; cyclic ethers such as dioxane; and esters such as methyl lactate, ethyl lactate (EL), methyl acetate, ethyl acetate, butyl acetate, methyl pyruvate, ethyl pyruvate, methyl methoxypropionate, and ethyl ethoxypropionate.

These solvents can be used individually, or in combination as a mixed solvent.

Further, among the mixed solvents, a mixed solvent obtained by mixing propylene glycol monomethyl ether acetate (PGMEA) with a polar solvent is preferable. The mixing ratio (weight ratio) of the mixed solvent can be appropriately determined, taking into consideration the compatibility of the PGMEA with the polar solvent, but is preferably from 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2.

Further, a mixed solvent of at least one of PGMEA and EL with γ-butyrolactone is also preferable. The mixing ratio (former:latter) of such a mixed solvent is preferably from 70:30 to 95:5.

The amount of the organic solvent (S) is not particularly limited, and is appropriately adjusted to a concentration which enables coating of a coating solution to a substrate, depending on the thickness of the coating film. In general, the organic solvent (S) is used in an amount such that the solid content of the resist composition becomes within the range from 2 to 20% by weight, and preferably from 5 to 15% by weight.

<Method of Forming a Resist Pattern>

The method of forming a resist pattern according to the third aspect includes: applying a positive resist composition of the present invention onto a substrate to form a resist film on the substrate; conducting exposure of the resist film; and developing the resist film to form a resist pattern.

Specifically, a resist pattern can be formed, for example, in the following manner. Firstly, the above-mentioned positive resist composition is applied to a substrate such as a silicon wafer using a spinner or the like, and a prebake (PAB) may be conducted if desired to form a resist film. Then, the formed resist film is selectively exposed using an exposure apparatus such as an EUV exposure apparatus through a mask pattern, or directly irradiating an electron beam without a mask pattern, and then PEB (Post Exposure Bake) is conducted.

Subsequently, developing is conducted using an alkali developing solution, and rising is conducted, thereby washing the developer on the substrate and the resist composition dissolved by the developer and drying to obtain a resist pattern.

The procedure as described above can be performed by any conventional methods. It is preferable that the operation conditions be appropriately selected depending on the formulation and properties of the positive resist composition.

The exposure source is not particularly limited, and radiations such as ArF excimer laser, KrF excimer laser, $F_2$ laser, extreme ultraviolet rays (EUV), vacuum ultraviolet rays (VUV), electron beam, X-rays, and soft X-rays can be used. The positive resist composition of the present invention is particularly effective to electron beam and EUV, especially electron beam.

If desired, a post exposure may be conducted following alkali developing. Further, an organic or inorganic anti-reflective film may also be provided between the substrate and the resist film.

As described hereinabove, by the compound (A1), positive resist composition containing the compound (A1) and method of forming a resist pattern using the positive resist composition according to the present invention, a resist pattern having reduced roughness can be formed.

The reason why the roughness is reduced is presumed as follows. The compound (A1) has a structure in which the polyhydric phenol compound (I) is the basic skeleton, and the phenolic hydroxyl groups thereof are protected with acid dissociable, dissolution inhibiting groups. As a result, a resist film obtained from a positive resist composition containing the compound (A1) exhibits a uniform dissolution behavior to a developing solution.

With respect to a conventional resist using a polymer as the base component, for example, in the spin coating process for forming a resist film, highly hydrophilic molecules and highly hydrophobic molecules are partially localized. As a result, fluctuation is generated in the distribution of each of the ingredients of the component (B) within the resist film. Further, in the polymer, fluctuation is generated in the distribution of the acid dissociable, dissolution inhibiting groups and the degree of dissociation. Therefore, it is presumed that the proceeding rate of the dissociation of the acid dissociable, dissolution inhibiting groups by the generation of acid (i.e., deprotection reaction rate) becomes heterogeneous at the interface between the exposed portion and the unexposed portion, the fluctuation is generated in the alkali solubility of the base components following the deprotection reaction, and fluctuation is generated in the dissolution rate of the resist film, thereby increasing the roughness.

On the other hand, in the present invention, as the compound (A1) has the aforementioned structure, it is presumed that there are small differences in the physical and chemical properties (molecular weight, hydrophilicity, polarity, and the like) between molecules. Especially, the distribution state of the acid dissociable, dissolution inhibiting groups is relatively uniform, which is considered to be contributing to the improvement in roughness. More specifically, the compound (A1) has a structure in which two benzene rings (inner-side benzene rings) are bonded to an aliphatic cyclic group as X at the center, and each of the two inner-side benzene rings has two benzene rings (outer-side benzene rings) via a carbon atom, and the each of the two inner-side benzene rings and the four outer-side benzene rings has at least one hydroxyl group. In this structure, due to a steric hindrance, it is presumed that acid dissociable, dissolution inhibiting groups are easily introduced to the hydroxyl groups bonded to the outer-side benzene rings (outer-side hydroxyl groups), as compared to the hydroxyl groups bonded to the inner-side benzene rings (inner-side hydroxyl groups). It is presumed that this steric hindrance effect is particularly large when the inner-side benzene rings have substituents such as alkyl groups and aromatic hydrocarbon groups on the ortho-positions thereof, as in compounds represented by general formula (I-1) shown above. By such a steric hindrance effect, it is considered that bias of position and number of the hydroxyl groups protected with the acid dissociable, dissolution inhibiting groups becomes small. As a result, it is presumed that the distribution state of the acid dissociable, dissolution inhibiting groups becomes relatively uniform, and the hydrophilicity and polarity also becomes uniform. For these reasons, a resist film obtained from a resist composition containing the compound (A1) exhibits uniform properties, and hence, the roughness can be reduced.

Further, a resist pattern formed by the method of the present invention exhibits excellent resolution.

EXAMPLES

As follows is a description of examples of the present invention, although the scope of the present invention is by no way limited by these examples.

Synthesis Example 1

Synthesis of 1,3-bis(2-formyl-6-methyl-4-hydroxyphenyl)-adamantane

In a 2-L four-necked flask, 615.6 g (5.4 mol) of trifluoroacetic acid was measured, and 126.0 g (0.9 mol) of hexamethylenetetramine was dropwise added and mixed at room temperature over 1 hour. Then, to the resulting mixture was intermittently added 104.4 g (0.3 mol) of 1,3-bis(2-methyl-4-hydroxyphenyl)-adamantane in the form of a powder at 70° C. over 1 hour, followed by stirring at 90° C. for 25 hours. Then, to the resulting reaction mixture, 210.0 g of water was added at 70° C., followed by stirring for 2 hours and 30 minutes while maintaining the temperature (wherein crystals were deposited while stirring). Thereafter, the resultant was cooled and neutralized with 16% by weight aqueous solution of sodium hydroxide. The neutralized liquid was elevated to 60° C., and 100 g of ethyl acetate was added thereto and cooled. Then, the resultant was filtered to obtain 126.8 g of crude crystals. Subsequently, the obtained crude crystals, 1,204.6 g of ethyl acetate and 150 g of water were charged into a 2-L four-necked flask, and the content of the flask was elevated to 70° C. and melted. Then, the resultant was allowed to stand for 10 minutes, followed by removing the water layer. Then, 100 g of water was added, and water washing and liquid separation were performed in the same manner. Thereafter, the resultant was concentrated under reduced pressure to remove 962.3 g of the solvent (wherein crystals were deposited during the concentration). The resulting concentrated product was cooled to 23° C., followed by filtration and drying, thereby obtaining 68.2 g of an object product which was a pale yellow powder (yield: 56.3%, based on 1,3-bis(2-methyl-4-hydroxyphenyl)adamantane).

With respect to the obtained object product, the properties thereof were analyzed, and the object product was identified. The results are shown below.

(Properties)
Purity: 95.5% (high performance liquid chromatography (HPLC))
Melting point: 182.5° C. (differential scanning calorimeter (DSC) peaktop)

(Identification)
Mass spectrometry: Liquid chromatography-mass spectroscopy (LC-MS) (Atmospheric Pressure Chemical Ionization (APCI))

Result: Molecular weight: 403 (M-H)–
$^1$H-NMR (400 MHz; solvent: DMSO-d6 (deuterated dimethylsulfoxide)

Result: As shown below

[Chemical Formula 21]

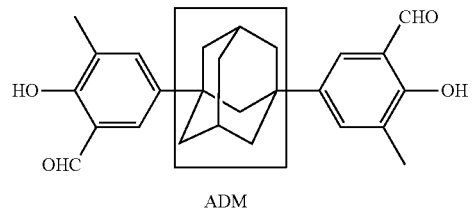

ADM

*The portion surrounded with a rectangle is designated as ADM

1H-NMR (400 MHz) identification results

| Shift value (ppm) | Number of protons | Signal | Assignment |
|---|---|---|---|
| 1.73 | 2 | s | —CH(ADM) |
| 1.84-1.94 | 10 | m | —CH$_2$(ADM) |
| 2.21 | 6 | s | —CH$_3$ |
| 2.25 | 2 | s | —CH$_2$(ADM) |
| 7.60 | 4 | s | Ph-H |
| 10.03 | 2 | s | —OH(Ph-OH) |
| 10.90 | 2 | s | —CHO |

Synthesis Example 2

Synthesis of polyhydric phenol compound (1) (1,3-bis{3-di(4-hydroxy-2,5-dimethylphenyl)methyl-6-methyl-4-hydroxyphenyl}-adamantane 16 g (0.13 mol) of 2,5-xylenol and 16 g of methanol were charged into a 500 ml four-necked flask, and 12.8 g of a hydrochloric acid gas was blown in at 30° C. Then, a solution obtained by dissolving 32.8 g (0.27 mol) of 2,5-xylenol in 71.2 g of methanol was dropwise added, followed by adding 32.3 g (0.08) mol of 1,3-bis(2-formyl-6-methyl-4-hydroxyphenyl)-adamantane at 25° C. over 1 hour 50 minutes to effect a reaction.

Thereafter, a reaction was performed while stirring at 40° C. for 3 hours.

Subsequently, the reaction product was neutralized with 87.8 g of 16% by weight aqueous solution of sodium hydroxide, and elevated to 60° C. Then, 137 g of toluene was added to the neutralized product and concentrated under atmospheric pressure to remove 98 g of the solvent. Then, 69 g of toluene was added to the resultant, followed by cooling and filtration to obtain 110 g of crude crystals. Thereafter the obtained crude crystals, 120 g of methyl isobutyl ketone and 60 g of water were charged into a 500 ml four-necked flask, and the content of the flask was elevated to 70° C. and melted. Then, the content of the flask was allowed to stand for 10 minutes, followed by removing the water layer. Then, 60 g of water was added, and water washing and liquid separation were performed in the same manner. Thereafter, the resultant was concentrated under atmospheric pressure to remove 96 g of the solvent, and 160 g of toluene was added. Then, the resulting concentrated product was cooled to 25° C., followed by filtration and drying, thereby obtaining 36.4 g of an object product (designated as "polyhydric phenol compound (1)") which was a pale yellow powder (yield: 53.1%, based on 1,3-bis(2-formyl-6-methyl-4-hydroxyphenyl)-adamantane). With respect to the obtained object product, the properties thereof were analyzed, and the object product was identified. The results are shown below.

(Properties)
Purity: 97.5% (HPLC)
Melting point: 275.8° C. (DSC peaktop)

(Identification)
Mass spectrometry: LC-MS (APCI)
Result: Molecular weight: 856 (M-H)–
$^1$H-NMR (400 MHz; solvent: DMSO-d6)
Result: As shown below

[Chemical Formula 22]

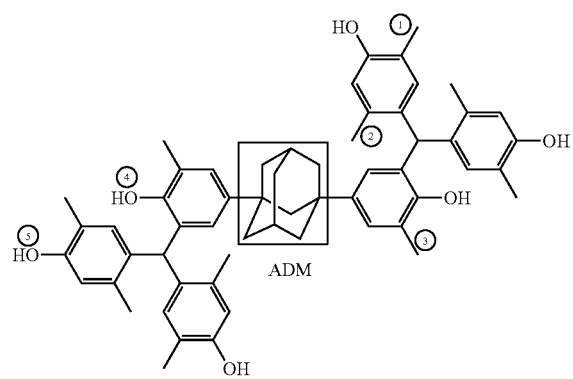

*The portion surrounded with a rectangle is designated as ADM

1H-NMR (400 MHz) identification results

| Shift value (ppm) | Number of protons | Signal | Assignment |
|---|---|---|---|
| 1.59-1.66 | 12 | m | —CH + —CH$_2$(ADM) |
| 1.92 | 12 | s | —CH$_3$(①) |
| 1.97 | 12 | s | —CH$_3$(②) |
| 2.07 | 2 | s | —CH$_2$(ADM) |
| 2.15 | 6 | s | —CH$_3$(③) |
| 5.74 | 2 | s | —CH |
| 6.36 | 4 | s | Ph-H(2,5-Xylenol) |
| 6.55 | 4 | s | Ph-H(2,5-Xylenol) |
| 6.56 | 2 | s | Ph-H |
| 6.85 | 2 | s | Ph-H |
| 7.90 | 2 | s | Ph-OH(④) |
| 8.84 | 4 | s | Ph-OH(⑤) |

Synthesis Example 3

Synthesis of Compound 5 g of the polyhydric phenol compound (1) synthesized in Synthesis Example 2 was dissolved in 20 g of tetrahydrofuran (THF), and 0.52 g of 60% by weight sodium hydride was added, followed by stirring for 10 minutes. Then, 3.68 g of 2-bromoacetic acid-2-methyladamantane was added, followed by stirring at room temperature for 10 hours.

Following the completion of the reaction, the product was extracted using a water/ethyl acetate system (water/ethyl acetate weight ratio=1:1). Then, the separated ethyl acetate solution was dried with sodium sulfate, followed by concentration under reduced pressure, thereby obtaining 5.3 g of a compound (A)-1 represented by formula (2) shown below.

[Chemical Formula 23]

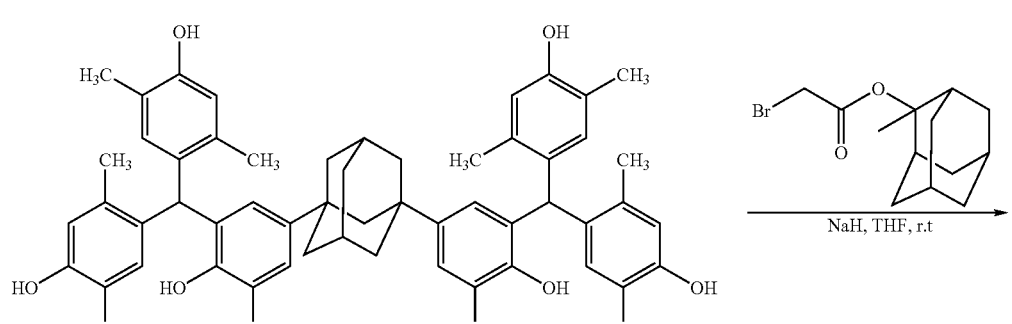

-continued

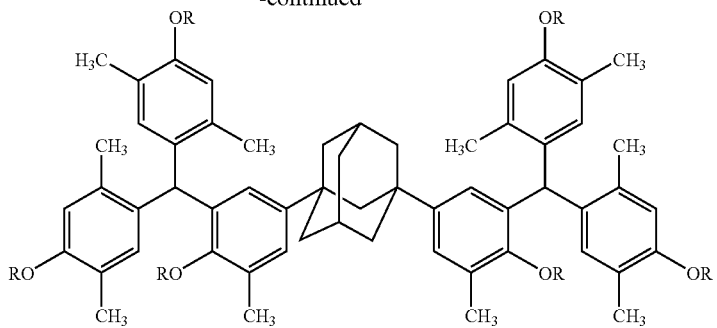

(2)

wherein each R represents a hydrogen atom or a group represented by formula (3) shown below:

[Chemical Formula 24]

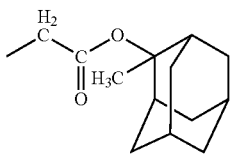

(3)

With respect to the compound (A)-1, the results of $^1$H-NMR (isotopic hydrogen nuclear magnetic resonance) spectroscopy are shown below. From the results, the protection ratio of the compound (A)-1 (the ratio (mol %) of R in formula (2) which is represented by the group represented by formula (3) above) was 31.1 mol %.

$^1$H-NMR data (deuterated dimethylsulfoxide (DMSO); internal standard: tetramethylsilane): δ 8.70-8.90 m 1.60H, 7.81-8.00 m 1.52H, 6.37-6.92 m 12H, 5.70-5.88 m 2H, 4.60-4.77 m 3.73H, 1.33-2.30 m 75.74H Example 1 and Comparative Example 1

The components shown in Table 1 were mixed together and dissolved to obtain positive resist composition solutions.

TABLE 1

| | Component (A) | Component (B) | Component (D) | Component (S) |
|---|---|---|---|---|
| Example 1 | (A)-1 [100] | (B)-1 [10] | (D)-1 [1] | (S)-1 [1,370] |
| Comparative Example 1 | (A)-2 [100] | (B)-1 [10] | (D)-1 [1] | (S)-1 [1,370] |

In Table 1, the values in brackets [ ] indicate the amount (in terms of parts by weight) of the component added.

(A)-2: polyhydroxystyrene (weight average molecular weight (Mw)=8,000; Mw/Mn=2.65) in which 30.7 mol % of the hydroxyl groups had been protected with 1-ethoxyethyl groups (B)-1: triphenylsulfonium nonafluorobutanesulfonate (D)-1: tri-n-octylamine (S)-1: a mixed solvent of PGMEA/EL=6/4 (weight ratio)

Subsequently, using the obtained positive resist composition solutions, evaluations were performed as follows. The results are shown in Table 2.

<Resolution>

Using a spinner, the positive resist composition solution was uniformly applied onto an 8 inch silicon substrate which had been treated with hexamethyldisilazane, and was subjected to a bake treatment (post applied bake: PAB) to obtain a resist film (film thickness: 150 nm).

Subsequently, the obtained resist film was patterned (exposed) with an electron beam lithography apparatus (HL-800D (VSB), manufactured by Hitachi Ltd.) with an accelerating voltage of 70 kV. Then, the resulting resist film was subjected to a bake treatment (post exposure bake: PEB) at the PEB temperature indicated in Table 2 for 90 seconds, and followed by developing in a 2.38% by weight aqueous solution of tetramethylammonium hydroxide (TMAH) for 60 seconds and rinsing in pure water for 30 seconds, thereby forming a line and space (L/S) pattern.

Using a scanning electron microscope S-9220 (manufactured by Hitachi Ltd.), the optimum exposure Eop (μC/cm$^2$) at which a 1:1 100 nm L/S pattern is formed, and the critical resolution at the Eop were determined.

<Surface Roughness>

Using a spinner, the positive resist composition solution was uniformly applied onto an 8 inch silicon substrate which had been treated with hexamethyldisilazane, and was subjected to a bake treatment (post applied bake: PAB) to obtain a resist film (film thickness: 150 nm).

Subsequently, the obtained resist film was exposed with an electron beam lithography apparatus (HL-800D (VSB), manufactured by Hitachi Ltd., accelerating voltage: 70 kV) with an exposure dose (μC/cm$^2$) sufficient to render the film thickness following developing about 80% of the initial film thickness, to thereby draw a large area (about 1 cm square). Then, the resulting resist film was subjected to a bake treatment (post exposure bake: PEB) at the PEB temperature indicated in Table 2 for 90 seconds, followed by developing in a 2.38% by weight aqueous solution of tetramethylammonium hydroxide (TMAH) for 60 seconds and rinsing in pure water for 30 seconds.

Following the rinsing, the surface of the resist film was observed by an atomic force microscope (AFM) (di Nano-Scope IV/D5000, manufactured by Veeco Instrument Inc.), and the root mean square roughness Rms (nm) per 1 μm square was determined.

TABLE 2

| | PEB temperature | Eop | Resolution | Surface roughness |
|---|---|---|---|---|
| Example 1 | 120° C. | 55 μC/cm² | 70 nm | 1.40 nm |
| Comparative Example 1 | 110° C. | 26 μC/cm² | 70 nm | 5.36 nm |

As seen from the results, with respect to the positive resist composition of Example 1 which used the compound (A)-1, the surface roughness was small. As the surface roughness was small, it meant that the roughness of the side walls of (line edge roughness: LER) of a resist pattern formed would be small. Also, the resolution was high.

On the other hand, with respect to the positive resist composition of Comparative Example 1 which used a resin, the surface roughness was extremely large. Therefore, LER would also be extremely poor.

INDUSTRIAL APPLICABILITY

The present invention provides a positive resist composition capable of forming a resist pattern with reduced roughness, a method of forming such a resist pattern, and a compound preferably used for the positive resist composition.

The invention claimed is:

1. A compound comprising a polyhydric phenol compound represented by general formula (I) shown below and having a molecular weight of 300 to 2,500, in which some or all of the hydrogen atoms of the phenolic hydroxyl groups are substituted with acid dissociable, dissolution inhibiting groups:

[Chemical Formual 1]

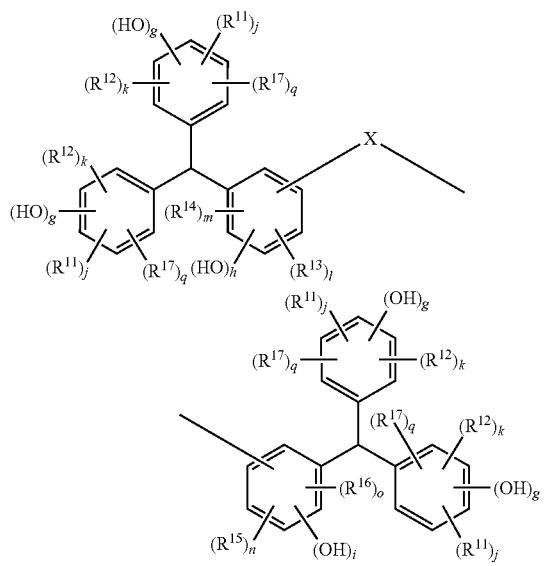

(I)

wherein $R^{11}$ to $R^{17}$ each independently represents an alkyl group of 1 to 10 carbon atoms or aromatic hydrocarbon group which may contain a hetero atom in the structure thereof; g and j each independently represents an integer of 1 or more, and k and q each independently represents 0 or an integer of 1 or more, with the proviso that g+j+k+q is 5 or less; h represents an integer of 1 or more, and l and m each independently represents 0 or an integer of 1 or more, with the proviso that h+l+m is 4 or less; i represents an integer of 1 or more, and n and o each independently represents 0 or an integer of 1 or more, with the proviso that i+n+o is 4 or less; and X represents an aliphatic cyclic group.

2. The compound according to claim 1, wherein said polyhydric phenol compound is represented by general formula (I-1) shown below:

[Chemical Formula 2]

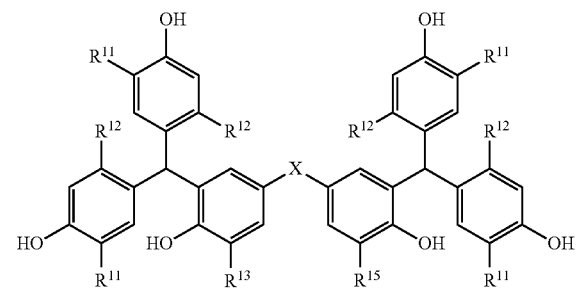

(I-1)

wherein each of $R^{11}$, $R^{12}$, $R^{13}$ and $R^{15}$ each independently represents an alkyl group of 1 to 10 carbon atoms or aromatic hydrocarbon group which may contain a hetero atom in the structure thereof; and X represents an aliphatic cyclic group.

3. The compound according to claim 1, wherein said acid dissociable, dissolution inhibiting groups are at least one member selected from the group consisting of alkoxycarbonylalkyl groups represented by general formula (p1) shown below and alkoxyalkyl groups represented by general formula (p2) shown below:

[Chemical Formula 3]

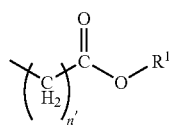

(p1)

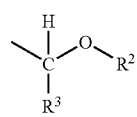

(p2)

wherein $R^1$ and $R^2$ each independently represents a linear, branched or cyclic alkyl group which may contain a hetero atom in the structure thereof; $R^3$ represents a hydrogen atom or a lower alkyl group; and n' represents an integer of 1 to 3.

4. A positive resist composition comprising a base component (A) which exhibits increased alkali solubility under action of acid and an acid generator component (B) which generates acid upon exposure, said base component (A) comprising a compound (A1) comprised of a polyhydric phenol compound represented by general formula (I) shown below and having a molecular weight of 300 to 2,500, in which some or all of the hydrogen atoms of the phenolic hydroxyl groups are substituted with acid dissociable, dissolution inhibiting groups:

[Chemical Formula 4]

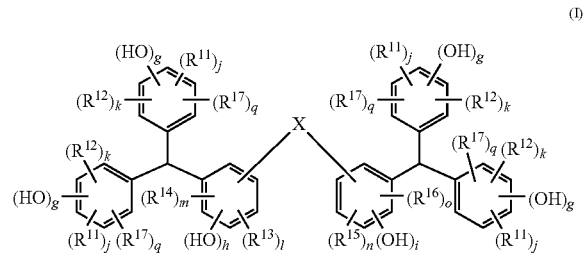

(I)

wherein $R^{11}$ to $R^{17}$ each independently represents an alkyl group of 1 to 10 carbon atoms or aromatic hydrocarbon group which may contain a hetero atom in the structure thereof; g and j each independently represents an integer of 1 or more, and k and q each independently represents 0 or an integer of 1 or more, with the proviso that g+j+k+q is 5 or less; h represents an integer of 1 or more, and l and m each independently represents 0 or an integer of 1 or more, with the proviso that h+l+m is 4 or less; i represents an integer of 1 or more, and n and o each independently represents 0 or an integer of 1 or more, with the proviso that i+n+o is 4 or less; and X represents an aliphatic cyclic group.

5. The positive resist composition according to claim 4, wherein said polyhydric phenol compound is represented by general formula (I-1) shown below:

[Chemical Formula 5]

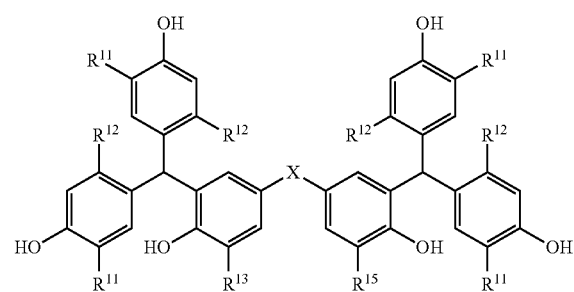

(I-1)

wherein each of $R^{11}$, $R^{12}$, $R^{13}$ and $R^{15}$ each independently represents an alkyl group of 1 to 10 carbon atoms or aromatic hydrocarbon group which may contain a hetero atom in the structure thereof; and X represents an aliphatic cyclic group.

6. The positive resist composition according to claim 4, wherein said base component (A) has acid dissociable, dissolution inhibiting groups which are at least one member selected from the group consisting of alkoxycarbonylalkyl groups represented by general formula (p1) shown below and alkoxyalkyl groups represented by general formula (p2) shown below:

[Chemical Formula 6]

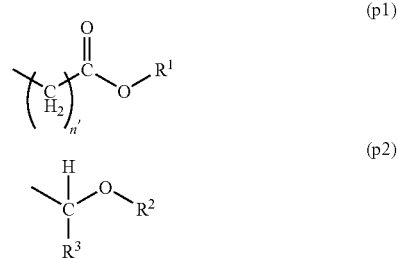

wherein $R^1$ and $R^2$ each independently represents a linear, branched or cyclic alkyl group which may contain a hetero atom in the structure thereof; $R^3$ represents a hydrogen atom or a lower alkyl group; and n' represents an integer of 1 to 3.

7. The positive resist composition according to claim 4, which further comprises a nitrogen-containing organic compound (D).

8. A method of forming a resist pattern, comprising: applying a positive resist composition of any one of claims 4 to 7 onto a substrate to form a resist film on the substrate; conducting exposure of said resist film; and developing said resist film to form a resist pattern.

\* \* \* \* \*